United States Patent [19]

Farquharson et al.

[11] Patent Number: 5,120,129
[45] Date of Patent: Jun. 9, 1992

[54] SPECTROSCOPIC CELL SYSTEM HAVING VENTED DUAL WINDOWS

[75] Inventors: Stuart Farquharson, Freeport; Leslie J. May, Lake Jackson; Terry D. Haymon, Brazoria, all of Tex.

[73] Assignee: The Dow Chemical Company, Midland, Mich.

[21] Appl. No.: 597,941

[22] Filed: Oct. 15, 1990

[51] Int. Cl.$^5$ .................... G01N 21/05; G01M 3/04
[52] U.S. Cl. .................... 356/246; 73/40; 73/46; 250/576; 356/440; 340/605
[58] Field of Search .................... 356/246, 410, 440; 250/576; 73/40, 40.7, 46, 49.8; 340/603, 605

[56] References Cited

U.S. PATENT DOCUMENTS

| | | |
|---|---|---|
| 570,726 | 11/1896 | Butts . |
| 1,779,076 | 10/1930 | Ray . |
| 3,177,706 | 4/1965 | Shuman et al. ............ 356/246 |
| 4,197,531 | 4/1980 | Wentworth, Jr. .......... 73/40 X |
| 4,283,937 | 8/1981 | Aoki et al. ............... 73/40.7 X |

FOREIGN PATENT DOCUMENTS

| | | |
|---|---|---|
| 3305982 | 8/1984 | Fed. Rep. of Germany ...... 356/246 |
| 3234198 | 9/1988 | Japan ....................... 73/46 |

Primary Examiner—Vincent P. McGraw
Attorney, Agent, or Firm—Timothy S. Stevens

[57] ABSTRACT

An improvement upon spectroscopic cells of the type that have a single window sealed to each window opening of the cell body. The improvement is: (1) to position an additional window at each such opening, each such window being juxtaposed, spaced apart and biplanar with each original window so that there is a sealed space between each additional window and each original window; and (2) to position at least two passageways through the body of the cell, each such passageway in fluid communication with each of the above formed sealed spaces so that any leakage of a sample past the original seal is vented from the cell via one of the passageways to a detector to be detected. In a highly preferred embodiment of the present invention each such sealed space contains a spacer ring and the body is provided with additional passageways so that a purge fluid, such as nitrogen, can be flowed through the passageways and the sealed space to a flow through detector, such as a thermal conductivity detector, to detect any leakage of a fluid sample past one of the original seals.

1 Claim, 2 Drawing Sheets

SPECTROSCOPIC CELL SYSTEM HAVING VENTED DUAL WINDOWS

FIELD OF THE INVENTION

The present invention is in the field of cells for spectroscopic analysis of fluid samples.

BACKGROUND OF THE INVENTION

U.S. Pat. No. 3,177,706 issued to Shuman et al. on Apr. 13, 1965 describes the general state of the art of spectroscopic cells for use in an industrial on-line analyzers. Such cells generally comprise a body defining a cavity therein, the body having two apertures therethrough in communication with the cavity. A window is sealed to each aperture. The cavity is filled with a fluid sample. Light is shown through one of the windows, through the sample, through the other window and then is directed to a photodetector.

A leak between the cell body and one of its windows in an industrial on-line analyzer can be a serious problem especially since such analyzers are usually not continuously attended. For example: (1) if the process stream is flammable, then there can be a fire or explosion hazard; or (2) if the process stream is toxic, then there can be a toxic release problem. It would be an advance in the art of on-stream chemical process analysis using spectroscopic cells if a cell system were developed that: (1) did not leak; or (perhaps more realistically) (2) that safely handled and detected any leak that did occur.

SUMMARY OF THE INVENTION

The present invention is an advance in the art of spectroscopic cells for on-stream spectrometric analysis because a means is disclosed to detect and/or safely handle such a seal leak.

The improvement of the present invention upon the above described spectroscopic cell is: (1) to position an additional window at each such aperture, each such window being juxtaposed, spaced apart and biplanar with each original window so that there is a sealed space between each additional window and each original window; and (2) to position at least two passageways through the body of the cell, each such passageway in fluid communication with each of the above formed sealed spaces so that any leakage of a sample past the original seal is vented from the cell via one of the passageways to a detector to be detected.

In a highly preferred embodiment of the present invention each such sealed space contains a spacer ring and the body is provided with additional passageways so that a purge fluid can be flowed through the passageways and the sealed space to a flow through detector to detect any leakage of a fluid sample past one of the original seals.

DETAILED DESCRIPTION OF THE INVENTION

Figure 1:
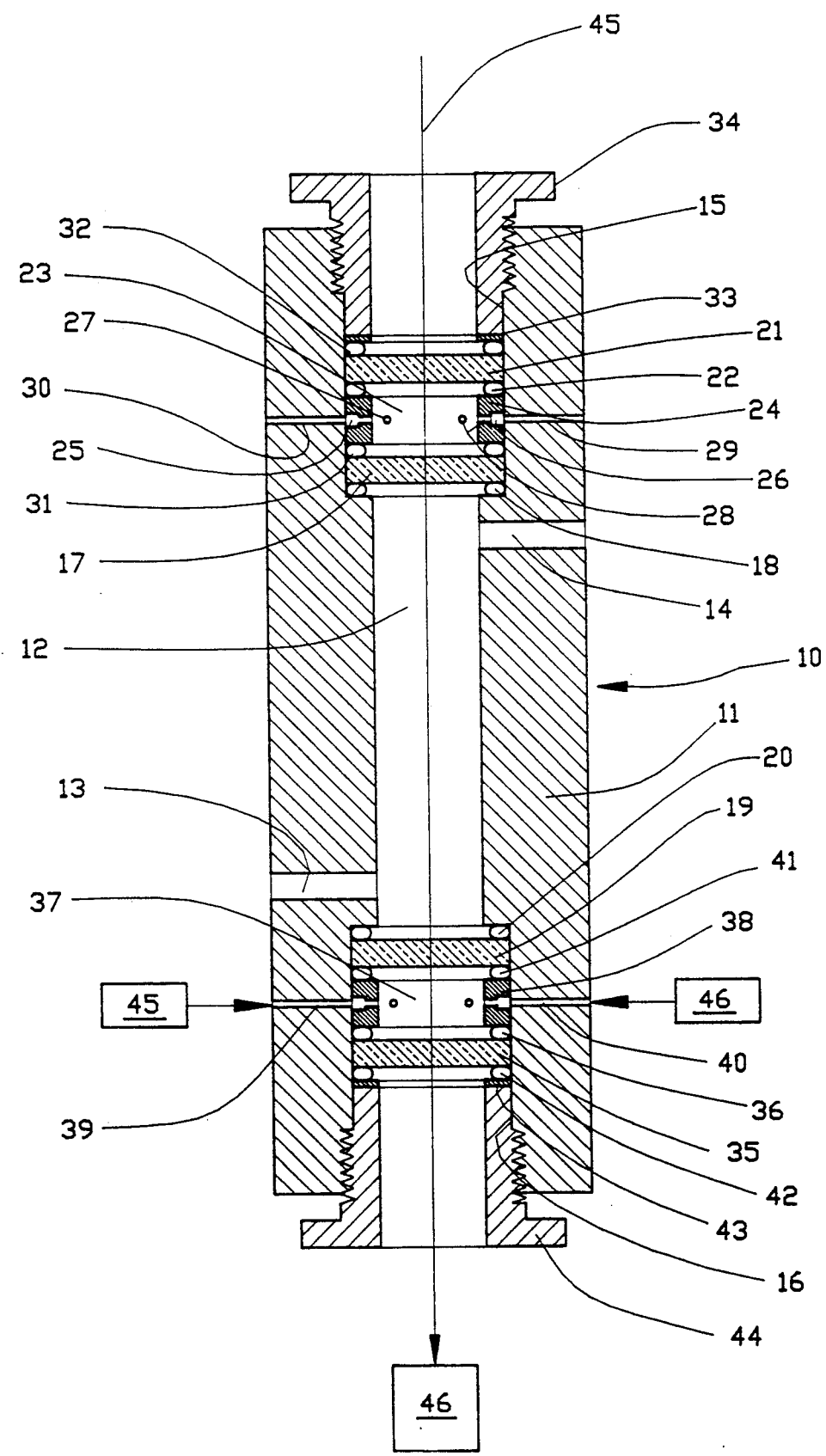
FIG. 1. is a side cross sectional view of a highly preferred embodiment of the present invention showing a cylindrical cell body having near each end thereof a spaced apart pair of windows and a purge ring between these windows.
Figure 2:
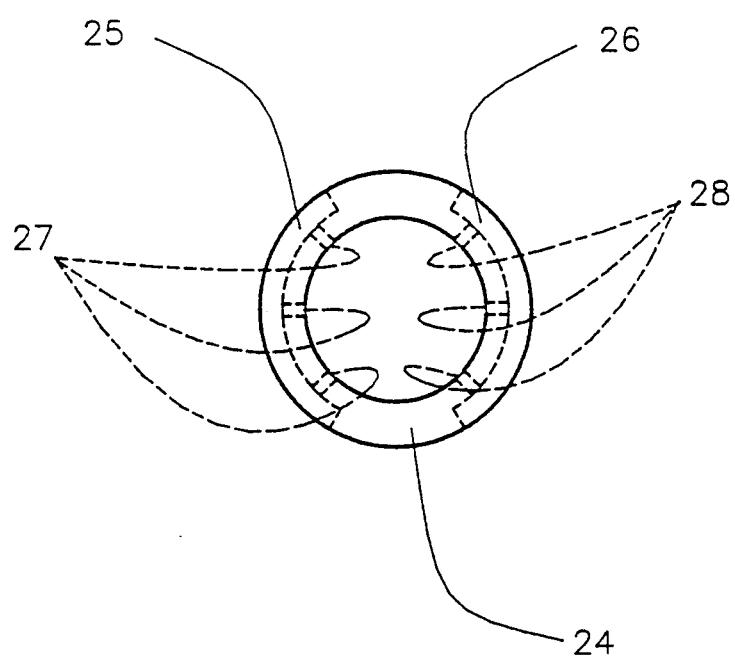
FIG. 2. is an end enlarged view of one of the purge rings showing by dotted lines a groove and six holes therein.

Referring now to FIG. 1, therein is shown a cross sectional side view of a highly preferred cell 10 of the present invention. The cell 10 has a body 11 defining a cavity 12 therein. The body 11 has a fluid sample inlet port 13 and a fluid sample outlet port 14 so that a fluid sample can be flowed into the port 13, to fill the chamber 12 and then flow out of the port 14. The body 11 also defines a first aperture 15 and a second aperture 16 therethrough in communication with the chamber 12. A first window 17 of transparent material such as sapphire is positioned in the first aperture 15. An O-ring 18 is the first seal means for sealing the window 17 to the aperture 15. A second window 19 of transparent material such as sapphire is positioned in the second aperture 16. An O-ring 20 is the second seal means for sealing the window 19 to the aperture 16. A third window 21 of transparent material such as sapphire is positioned in the first aperture 15. The third window 21 is juxtaposed, spaced apart and biplanar with the first window 17. An O-ring 22 is the third seal means for sealing the third window 21 to the first aperture 15 so that there is a first sealed space 23 between the first window 17 and the third window 21. Positioned within the first sealed space 23 is a first purge ring 24. The first purge ring 24 is also shown in FIG. 2 in an enlarged end view. Referring now to FIG. 1 and FIG. 2, the first purge ring 24 has a first groove 25 and a second groove 26 therein. The purge ring 24 has three passageways 27 therethrough in communication with the mouth of the purge ring 24 and the groove 25. The purge ring 24 also has three passageways 28 therethrough in communication with the mouth of the purge ring 24 and the groove 26. The body 11 has a first passageway 29 therethrough in fluid communication with the groove 26 which in turn, of course, is in fluid communication with the first sealed space 23 by way of the passageways 28. The body 11 also has a third passageway 30 therethrough in fluid communication with the groove 25 which in turn, of course, is in fluid communication with the first sealed space 23 by way of the passageways 27. An O-ring 31 compliments the O-ring 18 in sealing the first window 17 to the aperture 15. An O-ring 32 compliments the O-ring 22 in sealing the third window 21 in sealing the third window 21 to the aperture 15. A washer 33 is positioned between the O-ring 32 and a threaded bushing 34 which engages a complimentarily threaded portion of the aperture 15 of the body 11. When the bushing 34 is turned into the body 11, the bushing 34 pushes against the washer 33, the O-ring 32, the window 21, the O-ring 22, the ring 24, the O-ring 31, the window 17 and the O-ring 18 so that the O-rings are compressed and perform their respective sealing functions. A fourth window 35 of transparent material such as sapphire is positioned in the second aperture 16. The window 35 is juxtaposed, spaced apart and biplanar with the second window 19. An O-ring 36 is the fourth seal means for sealing the fourth window 35 to the second aperture 16 so that there is a second sealed space 37 between the second window 19 and the fourth window 35. Positioned within the second sealed space 37 is a second purge ring 38. The second purge ring 38 is identical in shape and function with the first purge ring 24. The body 11 has a fourth passageway 39 therethrough in fluid communication with the the second sealed space 37 by way of the groove and passageways of the second purge ring 38. The body 11 also has a second passageway 40 therethrough in fluid communication with the second sealed space 37 by way of the groove and passageways of the second purge ring 38. An O-ring 41 compliments the O-ring 20 in sealing the second window 19 to the aperture 16. An O-ring 42 compliments the O-ring 36 in sealing the fourth window 35 to the aperture 16. A washer 43 is positioned between the O-ring 42 and a threaded bushing 44 which engages a complimentarily threaded portion of the aperture 16 of the body 11. When the bushing 44 is turned into the body 11, the bushing 44 pushes against the washer 43, the O-ring 42, the window 35, the O-ring 35, the ring 40, the O-ring 41, the window 19 and the O-ring 20 so that the O-rings are compressed and perform their respective sealing functions. When a fluid sample is positioned in the cavity 12, then a beam of light 45 can be shown through the cell 10 to a photodetector 46.

If a fluid sample in the cavity 12 leaks past the O-rings 18 and 31 into the sealed space 23, then this leaking sample can be vented from the cell 10 by way of the first passageway 29 to a safe place. More preferably, a supply of purge fluid 45, such as a cylinder of compressed nitrogen, is used to flow the purge fluid into the fourth passageway 39 so that the purge fluid flows into the sealed space 37 and then out the second passageway 40. A flow through detector 46 is preferably in fluid communication with the second passageway 40 so that if a fluid sample in the cavity 12 leaks past the O-rings 20 and 41 into the sealed space 37, then this leaking sample can be purged from the cell 10 by way of the second passageway 29 to the detector 46 so that the leak can be detected. More preferably, of course, both ends of the cell 10 are purged and the purge fluid passed through a flow through detector.

It should be understood that the specific purge fluid of the present invention is not critical in the present invention and neither is its direction of flow through the purge ring. Further, the specific detector used to detect a leak is not critical in the present invention as long as it detects the leaking sample in the purge fluid. The purge fluid can be a gas and can be a liquid. Examples of suitable detectors in the present invention when the purge fluid is a gas are gas chromatography detectors such as thermal conductivity detectors, electron capture detectors, and ionization detectors. Examples of suitable detectors in the present invention when the purge fluid is a liquid are liquid chromatography detectors such as electrical conductivity detectors, dielectric constant detectors and spectrophotometric detectors. If the sample fluid is radioactive, then a radiation detector can be used.

The material of construction of the body 11 the purge ring 24 and the purge ring 38 is not critical in the present invention and can include plastics and metals. Preferably they are made of a corrosion resistant metal or metal alloy such as nickel, tantalum, Hastelloy C or stainless steel. The specific choice depends on the corrosiveness of the fluid sample.

The specific seal means used for the seals of the present invention is not critical and can include sealants, gaskets and lip seals. However, O-rings are preferred and fluoroelastomer O-rings, such as Viton and especially Kalrez O-rings, are highly preferred.

The specific material used for the windows of the present invention is not critical in the present invention and can include optical glass, quartz, fused silica, sapphire, silver chloride (for IR spectroscopy) and zinc selenide (also suited for IR spectroscopy). A cell suitable for liquid chlorine analysis by IR spectroscopy can be made of Hastelloy C while the silver chloride windows can be twenty five millimeters in diameter and four millimeters thick as available from Wilmad Glass, Buena, N.J.

The cell shown in FIG. 1 is a specific example of many that could have been described. It should be understood that variations upon the design of the cell shown in FIG. 1 can be made while staying within the scope of the present invention.

What is claimed is:

1. A cell system for spectroscopic analysis of fluid samples, comprising:
   (a) a body, the body defining a cavity therein for containing a fluid sample, the body defining a first aperture therethrough in communication with the cavity, the body at least also defining a second aperture therethrough in communication with the cavity;
   (b) a first window positioned near the first aperture;
   (c) a first seal means for sealing the first window to the first aperture;
   (d) a second window positioned near the second aperture;
   (e) a second seal means for sealing the second window to the second aperture;
   (f) a third window positioned near the first aperture, the third window being juxtaposed, spaced apart and biplanar with the first window;
   (g) a third seal means for sealing the third window to the first aperture so that there is a first sealed space between the first window and the third window;
   (h) a first purge ring positioned within the first sealed space;
   (i) a first passageway through the body in fluid communication with the first sealed space through the first purge ring;
   (j) a third passageway through the body in fluid communication with the first sealed space through the first purge ring;
   (k) a fourth window positioned near the second aperture, the fourth window being juxtaposed, spaced apart and biplanar with the second window;
   (l) a fourth seal means for sealing the fourth window to the second aperture so that there is a second sealed space between the second window and the fourth window;
   (m) a second purge ring positioned within the second sealed space;
   (n) a second passageway through the body in fluid communication with the second sealed space through the second purge ring;
   (o) a fourth passageway through the body in fluid communication with the second sealed space through the second purge ring;
   (p) a means for supplying a fluid under pressure in fluid communication with the fourth passageway; and
   (q) a flow through detector in fluid communication with the second passageway so that any leakage of a fluid sample from the cavity into the second sealed space can be carried to the flow through detector to be detected.

* * * * *